US009885080B2

(12) United States Patent
Gao et al.

(10) Patent No.: US 9,885,080 B2
(45) Date of Patent: Feb. 6, 2018

(54) KIT, A DEVICE AND A METHOD FOR DETECTING COPY NUMBER OF FETAL CHROMOSOMES OR TUMOR CELL CHROMOSOMES

(75) Inventors: Yang Gao, Beijing (CN); Daixing Zhou, Beijing (CN); Jianguang Zhang, Beijing (CN); Feng Tian, Beijing (CN)

(73) Assignee: BERRY GENOMICS CO., LTD., Beijing (CN)

( * ) Notice: Subject to any disclaimer, the term of this patent is extended or adjusted under 35 U.S.C. 154(b) by 948 days.

(21) Appl. No.: 13/811,634

(22) PCT Filed: May 31, 2011

(86) PCT No.: PCT/CN2011/075037
§ 371 (c)(1),
(2), (4) Date: Jan. 22, 2013

(87) PCT Pub. No.: WO2012/162884
PCT Pub. Date: Dec. 6, 2012

(65) Prior Publication Data
US 2013/0130921 A1    May 23, 2013

(51) Int. Cl.
C12Q 1/68 (2006.01)
G06F 19/20 (2011.01)
(52) U.S. Cl.
CPC ......... *C12Q 1/6874* (2013.01); *C12Q 1/6809* (2013.01); *C12Q 1/6869* (2013.01); *G06F 19/20* (2013.01)
(58) Field of Classification Search
None
See application file for complete search history.

(56) References Cited

U.S. PATENT DOCUMENTS

| 2010/0112575 A1* | 5/2010 | Fan ...................... C12Q 1/6883 435/6.11 |
| 2010/0112590 A1 | 5/2010 | Lo et al. |
| 2010/0216153 A1 | 8/2010 | Lapidus et al. |

FOREIGN PATENT DOCUMENTS

| CN | 102018406 A | 6/2011 |
| WO | 2010/033578 A2 | 3/2010 |
| WO | 2011/051283 A1 | 5/2011 |

OTHER PUBLICATIONS

Fan et al., "Analysis of the Size Distributions of Fetal and Maternal Cell-Free DNA by Paired-End Sequencing", Clinical Chemistry, 56:8, p. 1279-1286 (2010).*

(Continued)

*Primary Examiner* — Karen S. Weiler
(74) *Attorney, Agent, or Firm* — Porter Wright Morris & Arthur LLP

(57) ABSTRACT

The invention relates to a kit, a device and a method for detecting the copy number of fetal chromosomes and tumor cell chromosomes. The method for detecting the copy number of fetal chromosomes or tumor cell chromosomes of the invention includes the following steps: collecting maternal plasma or plasma of tumor patient; separating the plasma from blood cells in blood; preparing Deoxyribonucleic Acids (DNA) in the plasma into a sequencing library; sequencing the DNA sequencing library; comparing a sequencing result with a genomic sequence map to determine which chromosome the DNA sequence comes from and the length of each DNA sequence; and calculating the ratio of the DNA segments from the chromosomes to be detected to all DNA segments in the same sample by a sequencing and comparison result of DNA, correcting the ratio according to a GC content of the DNA segments from the chromosomes to be detected, and calculating the variation of the corrected ratio of the DNA segments from the (Continued)

chromosomes to be detected in a sample to be detected, and determining the copy number of the chromosomes to be detected according to degree of variation.

10 Claims, 14 Drawing Sheets

(56) References Cited

OTHER PUBLICATIONS

Rossa W.K. Chu et al, Maternal Plasma DNA Analysis with Massively Parallel Sequencing by Ligation for Noninvasive Prenatal Diagnosis of Trisomy 21, Clinical chemistry, 56(3):459-463 (2010, published online Dec. 21, 2009).

European Search Report from corresponding European Application No. 11866914.2, dated Oct. 27, 2014.

Chiu et al., Non-invasive prenatal testing of fetal whole chromosome aneuploidy by massively parallel sequencing, Proceedings of the National Academy of Sciences, 105(51):20458-20463 (Dec. 10, 2008), and supporting information, pp. 1-17.

Sehnert et al., Optimal Detection of Fetal Chromosomal Abnormalties by Massively Parallel DNA Sequencing of Cell-Free Fetal DNA from Maternal Blood, Clinical Chemistry, 57(7):1042-1049 (2011).

Jorgez et al., Improving Enrichment of Circulating Fetal DNA for Genetic Testing: Size Fractionation Followed by Whole Gene Amplification, Fetal Diagnosis and Therapy, 25(3):314-319 (Jan. 1, 2009).

Liang et al., Non-invasive prenatal testing of fetal whole chromosome aneuploidy by massively parallel sequencing, Prenatal Diagnosis, 33(5):409-415 (May 9, 2013).

* cited by examiner

KIT, A DEVICE AND A METHOD FOR DETECTING COPY NUMBER OF FETAL CHROMOSOMES OR TUMOR CELL CHROMOSOMES

FIELD OF THE INVENTION

The invention relates to a kit, a device and a method for detecting the copy number of fetal chromosomes or tumor cell chromosomes.

BACKGROUND OF THE INVENTION

The copy number abnormality of chromosomes is closely linked with human diseases. The chromosome abnormality occurs in fetal cells carried with genetic disease and tumor cells. On average, 9 of 1000 newborns may carry diseases caused by copy number abnormality of chromosomes (1). Therefore, it is important to detect the copy number of chromosomes before children have not been born yet. However, currently used diagnosis methods including amniocentesis and ovine chorionic belong to invasive methods, which bring certain risks to pregnant women and fetuses. Serum protein markers and ultrasonic waves are used for detecting whether the fetuses suffer diseases due to copy number abnormality of chromosomes, although it is noninvasive, pathogenic factors are not detected directly, so the accuracy and sensitivity is not good (2). There is also a problem that the diseases due to the copy number abnormality of chromosomes cannot be found as soon as possible. This situation prompts researchers to develop an accurate and highly sensitive noninvasive diagnosis and detection method.

Since fetal DNA in maternal blood have been found (3), diagnosing and detecting the abnormality of fetal chromosomes noninvasively and directly becomes an important study topic. In 2007, Professor LO Yuk Ming Dennis and his colleagues proved that the percentage of mutation site of placenta specific gene 4 in maternal plasma mRNA could be used for judging whether the fetus has chromosome 21 which was a triploid (4). The percentage of mutation site is at the same time used for judging whether chromosome 18 is a triploid (5). Its limitation is in that the mutation site is not common in the crowd, so these methods are only suitable for a part of crowd. During the same period, digital PCR (dPCR) is used for detecting the triploid of fetal chromosome (6), (7). The digital PCR has the advantage of independency of any mutation site, but its accuracy is insufficient, and requires many blood samples, which increases sampling difficulty.

In recent years, the above problems have been solved by rapidly developed high-throughput DNA sequencing techniques. These techniques include Genome Analyzer of Illumina (8), SOLiD of Life Technologies (9) and Heliscope of Helicos (10), by which hundreds of millions or even billions of sequences can be detected once. When these techniques are used for detecting DANs in maternal plasma, the change of the number of chromosomes of trace amounts of fetal DNA in plasma can be detected (11), (12), (13). But due to high sequencing cost, these techniques have not been used commonly. At the same time, there is still an unsolved problem of detecting the change of partial copy number of fetal chromosomes from maternal plasma. It is advantageous to detect the change of copy number of fetal chromosomes from maternal plasma by high-throughput sequencing, but this technique is expensive in cost and cannot be popularized. Moreover, the sequencing Coefficient Of Variation (CV) is high, and the detecting accuracy and stability also needs to be improved. The sequencing CV also decides that this method is only suitable for a few chromosomes, such as chromosome 21, chromosome 18, and unsuitable for detecting the change of partial copy number of chromosomes.

It is very expensive and difficult to detect the change of the number of chromosomes by high-throughput sequencing, the main reason is that the content of fetal DNA in maternal plasma is low, only 5% when it is low, in particular during early fetal development. Most DNA in maternal plasma is maternal DNA. The background of maternal DNA easily encompasses the change of the number of fetal chromosomes or partial copy number. Therefore, the method for separating the pregnant women and fetal DNA becomes the subject studied for years with little progress. A successful method should belong to histone separation method invented by Baylor Medical College (14). The quantity of DNA separated is very small, so the method is only suitable for detecting the mutation site, unsuitable for detecting the change of the copy number of chromosomes.

SUMMARY OF THE INVENTION

In view of the above problems in the method for detecting the copy number of fetal chromosomes, the inventor designs a kit, a device and a method for detecting the whole or partial copy number of fetal chromosomes effectively at low cost.

The invention is based on the following facts: the inventor finds that the GC contents of the DNA segments from each chromosome respectively have linear relationships with the ratios of the DNA segments from each chromosome to the total DNA segments, the above phenomena may be related to the detection method, the linear relationship can be represented by y=ax+b, where y represents the GC content of the DNA segment from to the chromosome to be detected, x represents the ratio of the number of the DNA segments from the chromosome to be detected to the total DNA, a and b are constants, a and b may be different values for different chromosomes, the ratio can be corrected according to the GC content of the DNA segments from the chromosomes to be detected, and the variation of the corrected ratio of the DNA segments from the chromosomes to be detected in the sample to be detected is calculated, and the copy number of the chromosomes to be detected is determined according to degree of variation. By correcting the GC content, many false negative results that cannot be detected only by judgment method of the ratio of the DNA segments of each chromosome to total DNA segments can be detected effectively. The specific experiments are taken as evidences in the detailed description of the embodiments.

Additionally, as reported in the document (15), most fetal DNA in maternal plasma are 100 bp to 250 bp segments, particularly in the great majority of 150 bp to 170 bp. Although only a tiny part of maternal DNA are distributed in the segment range, the DNA segments of more than 250 bp basically belong to maternal DNA. The inventor finds that, although the reason is unknown, the ratio of the DNA segments from each chromosome to the total DNA segments is uniformly distributed with length at any point or in any interval within the range of 100 bp to 250 bp, i.e., each chromosome is with length at any point within the range of 100 bp to 250 bp, such as 110 bp or 167 bp (the quantity of DNA in the site is the most), the ratio with the total DNA represents the ratio of other points, thus representing the ratio of each chromosome to all DNA within the range of 100 bp to 250 bp. Through sequencing the DNA with length at any point or in any interval within the range of 100 bp to 250 bp in the DNA, the sequencing results of all DNA with length at any point or in any interval within the range of 100 bp to 250 bp in the DNA are compared with the genomic sequence map to determine which chromosome each DNA segment of the DNA sequence of all DNA or in any interval within the range of 100 bp to 250 bp in the DNA comes from and the length of each DNA segment; the ratio of the number of the DNA segments from the chromosomes to be detected in all DNA with length at any point or in any interval within the range of 100 bp to 250 bp in the same sample to all DNA segments with length at any point or in any interval within the range of 100 bp to 250 bp is to calculated to obtain the ratio of each fetal chromosomes to the total DNA. This greatly reduces the detecting results. The ratio is corrected according to the GC content of the DNA segments from the chromosomes to be detected in conjunction with the above GC-based correction method, and the variation of the corrected ratio of the DNA segments from the chromosomes to be detected in the sample to be detected is calculated to determine the copy number of the chromosomes to be detected according to degree of variation.

At the same time, the inventor finds that, similarly during the development of tumors, the same thing happens in the blood from patient as in the maternal blood during the development of tumors, i.e., in the blood of tumor patient, DNA of free tumor cells can be detected. The linear relationship between the GC content of the DNA segments from each chromosome measured with the method of the invention with the ratios of the DNA segments from each chromosome to the total DNA segments is similarly suitable for detecting aneuploidy of tumor cells. Moreover, DNA of free tumor cells in plasma are present in the form of nucleosomes, so they are mostly 100 bp to 250 bp segments, the ratio of the DNA segments from each chromosome to the total DNA segments is uniformly distributed with length at any point or in any interval within the range of 100 bp to 250 bp, i.e., each chromosome is with length at any point within the range of 100 bp to 250 bp, thus representing the ratio of each chromosome to all DNA within the range of 100 bp to 250 bp. Therefore, the kit, the device and the method of the invention are also suitable for detecting the copy number of tumor cell chromosomes or partial chromosomes.

Based on the above findings, the inventor provides a kit, a device and a method for detecting the copy number of fetal chromosomes or tumor cell chromosomes or partial chromosomes non-invasively and economically.

A kit for detecting the copy number of fetal chromosomes or tumor cell chromosomes provided by the invention includes: an instrument for collecting blood from a pregnant women or a tumor patient; an instrument for separating blood cells from plasma in blood; a reagent and an instrument for extracting Deoxyribonucleic Acids (DNA) in the plasma; a reagent and an instrument for separating the DNA with a physical method according to the size of the DNA segments; and a reagent and an instrument for sequencing DNA with length with length at any point or in any interval within the range of 100 bp to 250 bp.

Preferably, the fetal chromosomes or tumor cell chromosomes are the whole chromosomes or partial chromosomes.

Preferably, the kit of the invention further includes: a reagent and an instrument for preparing all DNA into a sequencing library.

Preferably, the kit of the invention further includes: a reagent and an instrument for performing PCR amplification of the DNA extracted from plasma or the sequencing library.

Preferably, the DNA with length at any point or in any interval within the range of 100 bp to 250 bp is the 150 bp-170 bp DNA, more preferably, is the 167 bp DNA.

Another kit for detecting the copy number of fetal chromosomes or tumor cell chromosomes provided by the invention includes: an instrument for collecting blood from a pregnant women or a tumor patient; an instrument for separating blood cells from plasma in blood; a reagent and an instrument for extracting DNA from the plasma; a reagent and an instrument for preparing the DNA into a sequencing library; and a reagent and an instrument for sequencing the DNA, wherein the fetal chromosomes or tumor cell chromosomes are the whole chromosomes or partial chromosomes.

Preferably, the kit of the invention further includes: a reagent and an instrument for performing PCR amplification on the DNA extracted from plasma.

A device for detecting the copy number of fetal chromosomes or tumor cell chromosomes provided by the invention includes: a detecting module, which is used for sequencing DNA in a sample of maternal plasma or plasma of tumor patient, wherein the sequencing includes preparing all DNA in the sample of maternal plasma or plasma of tumor patient into a sequencing library; a comparison module, which is used for comparing a sequencing result of the DNA with a genomic sequence map to determine which chromosome each DNA sequence comes from and the length of each DNA sequence; a calculating module, which is used for calculating the ratio of the number of DNA segments from the chromosomes to be detected to the total number of DNA segments in the same sample, correcting the ratio according to a GC content of the DNA segments from the chromosomes to be detected, and calculating the variation of the corrected ratio of the DNA segments from the chromosomes to be detected in a sample to be detected, and determining the copy number of the chromosomes to be detected according to degree of variation; and an output module, which is used for outputting the copy number of the chromosomes to be detected.

Preferably, the calculating module in the device of the invention corrects the ratios of the chromosomes 2, 3, 4, 5, 6, 7, 8, 12, 13, 18 and X according to the following function: the GC contents of the DNA segments from the chromosomes 2, 3, 4, 5, 6, 7, 8, 12, 13, 18 and X respectively have linear relationships with the ratios of the DNA segments from each chromosome to the total DNA segments, the linear relationship can be represented by $y=ax+b$, where y represents the GC content of the DNA segment from the chromosome to be detected, x represents the ratio of the number of the DNA segments from the chromosome to be detected to the total DNA, a and b are constants, and a is negative.

Preferably, the linear relationship between the GC contents of the DNA segments from the chromosomes 2, 3, 4, 5, 6, 7, 8, 12, 13, 18 and X and the ratios of the DNA segments from each chromosome to the total DNA segments is as shown in Table 1.

Preferably, the calculating module in the device of the invention corrects the ratios of the chromosomes 1, 9, 10, 11, 15, 16, 17, 19, 20, 21 and 22 according to the following function: the GC contents of the DNA segments from the chromosomes 1, 9, 10, 11, 15, 16, 17, 19, 20, 21 and 22 respectively have linear relationships with the ratios of the DNA segments from each chromosome to the total DNA segments, the linear relationship can be represented by $y=ax+b$, where y represents the GC content of the DNA segment from the chromosome to be detected, x represents the ratio of the number of the DNA segments from the chromosome to be detected to the total DNA, a and b are constants, and a is positive.

Preferably, the linear relationship between the GC contents of the DNA segments from the chromosomes 1, 9, 10, 11, 15, 16, 17, 19, 20, 21 and 22 and the ratios of the DNA segments from each chromosome to the total DNA segments is as shown in Table 2.

Preferably, the sequencing includes the process of preparing all DNA in the sample of maternal plasma or plasma of tumor patient into a sequencing library.

Preferably, sequencing the DNA in the sample of maternal plasma or plasma of tumor patient is performed by paired-end short sequence sequencing, single-end long sequence sequencing or single-end short sequence sequencing.

Preferably, the fetal chromosomes or tumor cell chromosomes are the whole chromosomes or partial chromosomes.

Preferably, the PCR amplification of the DNA in the sample of maternal plasma or plasma of tumor patient is performed DNA before sequencing.

Preferably, in the device of the invention, the calculating module is used for calculating the ratio of the number of the DNA segments from the chromosomes to be detected in all DNA with length at any point or in any interval within the range of 100 bp to 250 bp in the same sample to the total number of all DNA segments with length at any point or in any interval within the range of 100 bp to 250 bp, correcting the ratio according to the GC content of the DNA segments from the chromosomes to be detected in all DNA with length at any point or in any interval within the range of 100 bp to 250 bp, and calculating the variation of the corrected ratio of the DNA segments from the chromosomes to be detected in the sample to be detected, and determining the copy number of the chromosomes to be detected according to degree of variation.

Preferably, all DNA with length at any point or in any interval within the range of 100 bp to 250 bp in the sample of maternal plasma or plasma of tumor patient are prepared into the sequencing library.

Preferably, the PCR amplification of the DNA in the sample of maternal plasma or plasma of tumor patient is performed DNA before or after being prepared into the sequencing library.

Preferably, the DNA with length at any point or in any interval within the range of 100 bp to 250 bp is the 150 bp-170 bp DNA, more preferably the 167 bp DNA.

A method for detecting the copy number of fetal chromosomes or tumor cell chromosomes provided by the invention includes the following steps: collecting maternal plasma or plasma of tumor patient; separating the plasma from blood cells in blood; preparing DNA in the plasma into a sequencing library; sequencing the DNA sequencing library; comparing a sequencing result with a genomic sequence map to determine which chromosome each DNA sequence comes from and the length of each DNA segment; and calculating the ratio of the DNA segments from the chromosomes to be detected to the total number of the DNA segments by sequencing and comparison results of DNA, correcting the ratio according to a GC content of the DNA segments from the chromosomes to be detected, and calculating the variation of the corrected ratio of the DNA segments from the chromosomes to be detected in a sample to be detected, and determining the copy number of the chromosomes to be detected according to degree of variation.

Preferably, the method of the invention further includes correcting the ratios of the chromosomes 2, 3, 4, 5, 6, 7, 8, 12, 13, 18 and X according to the following function: the GC contents of the DNA segments from the chromosomes 2, 3, 4, 5, 6, 7, 8, 12, 13, 18 and X respectively have linear relationships with the ratios of the DNA segments from each chromosome to the total DNA segments, the linear relationship can be represented by $y=ax+b$, where y represents the GC content of the DNA segment from the chromosome to be detected, x represents the ratio of the number of the DNA segments from the chromosome to be detected to the total DNA, a and b are constants, and a is negative.

Preferably, the linear relationship between the GC contents of the DNA segments from the chromosomes 2, 3, 4, 5, 6, 7, 8, 12, 13, 18 and X and the ratios of the DNA segments from each chromosome to the total DNA segments is as shown in Table 1.

Preferably, the method of invention further includes correcting the ratios of the chromosomes 1, 9, 10, 11, 15, 16, 17, 19, 20, 21 and 22 according to the following function: the GC contents of the DNA segments from the chromosomes 1, 9, 10, 11, 15, 16, 17, 19, 20, 21 and 22 respectively have linear relationships with the ratios of the DNA segments from each chromosome to the total DNA segments, the linear relationship can be represented by $y=ax+b$, where y represents the GC content of the DNA segment from the chromosome to be detected, x represents the ratio of the number of the DNA segments from the chromosome to be detected to the total DNA, a and b are constants, and a is positive.

Preferably, the linear relationship between the GC contents of the DNA segments from the chromosomes 1, 9, 10, 11, 15, 16, 17, 19, 20, 21 and 22 and the ratios of the DNA segments from each chromosome to the total DNA segments is as shown in Table 2.

Preferably, the method includes calculating the ratio of the number of the DNA segments from the chromosomes to be detected in all DNA with length at any point or in any interval within the range of 100 bp to 250 bp in the same sample to the total number of all DNA segments with length at any point or in any interval within the range of 100 bp to 250 bp only by sequencing and comparison results of all DNA with length at any point or in any interval within the range of 100 bp to 250 bp, correcting the ratio according to the GC content of the DNA segments from the chromosomes to be detected in all DNA with length at any point or in any interval within the range of 100 bp to 250 bp, and calculating the variation of the corrected ratio of the DNA segments from the chromosomes to be detected in the sample to be detected, and determining the copy number of the chromosomes to be detected according to degree of variation.

Preferably, sequencing the DNA sequencing library is performed by paired-end short sequence sequencing, single-end long sequence sequencing or single-end short sequence sequencing.

Preferably, the DNA with length at any point or in any interval within the range of 100 bp to 250 bp is the 150 bp-170 bp DNA, more preferably the 167 bp DNA.

BRIEF DESCRIPTION OF THE DRAWINGS

FIG. 5G shows a standard curve of the 19-th to the 22-th chromosomes, FIG. 5H shows a standard curve of X chromosome. The functions of standard curves of each chromosome are as shown in Table 1 and Table 2.

DETAILED DESCRIPTION OF THE EMBODIMENTS

Figure 1:
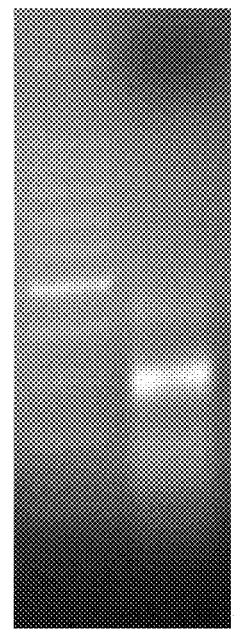
FIG. 1 is an image obtained by 1% agarose gel electrophoresis after preparing the DNA in maternal plasma into a library for paired-end sequencing. Left channel is an image of DNA 100 bp marker, right channel is an image of library for paired-end sequencing, and the most obvious stripe is located at about 280 bp, containing 120 bp connecting primers.

It should be noted that, without contradiction, the embodiments in the application and the characteristics in the embodiments can be combined. The invention is described below with reference to drawings in conjunction with embodiments. The drawings of the invention and the embodiments are only used for explaining the invention, and not intended to limit the invention.

Term Definition

Paired-end short sequence refers to a sequence of less than 50 bp next to 5'-terminal connecting primer and a sequence of less than 50 bp next to 3'-terminal connecting primer. Preferably, paired-end short sequence refers to a sequence of not more than 36 bp next to 5'-terminal connecting primer and a sequence of not more than 36 bp next to 3'-terminal connecting primer.

Single-end short sequence refers to a sequence of less than 50 bp next to 5'-terminal connecting primer or a sequence of less than 50 bp next to 3'-terminal connecting primer. Preferably, single-end short sequence refers to a sequence of not more than 36 bp next to 5'-terminal connecting primer or a sequence of not more than 36 bp next to 3'-terminal connecting primer.

Single-end long sequence refers to a sequence of more than 99 bp next to 5'-terminal connecting primer or a sequence of more than 99 bp next to 3'-terminal connecting primer.

Paired-end sequencing refers to testing the sequence at both ends of the sequence.

Single-end sequencing refers to testing the sequence at one end of the sequence.

DNA cluster refers to multiple DNA molecules formed by amplifying one DNA molecule and located in one fixed surface area. In the embodiments of the application, DNA cluster refers to about 1000 DNA molecules formed by amplifying one DNA molecule and located within 1 square micron.

Emulsion Polymerase Chain Reaction (PCR) refers to performing PCR reaction by placing PCR reactants including PCR template DNA, PCR primer, PCR polymerase and free bases within one oil droplet. Usually, within one oil droplet, the template of emulsion PCR has only one DNA molecule.

GC content refers to the ratio of the number of guanine and cytosine to the total number of all bases in nucleic acids or deoxyribonucleic acids.

Embodiment 1: A Method for Detecting the Copy Number of Fetal Chromosomes

Step 1: Collecting maternal blood to prepare plasma.

In the embodiment, 14 maternal blood samples are extracted, sample codes: G356, G397, G426, G735, G756, G760, G763, G770, G778, G779, G780, G781, G824 and G825, all identified as normal female fetus samples [46, XX] by Professor Wu Lingqian of Xiangya Medical College of Central South University through amniocentesis by chromosome karyotype. The detected data of the above samples are used for drawing a standard curve, and the above samples are also used as standard samples. Plasma samples from which blood cells are removed are obtained after centrifuging the blood samples at high speed, and each sample has a plasma volume of about 1 ml.

Step 2: Extracting plasma DNA.

DNA in the plasma is extracted by using DNA extraction kit produced by Qiagen (product number: 57704).

Step 3: Preparing the plasma DNA into a sequencing library.

The plasma DNA can be prepared into a library for paired-end short sequence sequencing, single-end long sequence sequencing or single-end short sequence sequencing. The process for preparing the library for paired-end short sequence sequencing is as follows.

The extracted DNA is end-blunted and subjected to 5'-terminal phosphorylation: 30 µl of DNA, 45 µl of pure water, 10 µl of T4 DNA ligase buffer with 10 mM ATP, 4 µl of 10 mM dNTP Mix, 5 µl of T4 DNA polymerase, 1 µl of Klenow enzyme and 5 µl of T4 PNK are treated in a warm bath for 30 min at 20 after mixing (the reagents are provided by Illumina sample preparation kit PE-102-1001). The DNA is purified by QIAGEN QIAquick PCR purification kit (part #28104) after warm bath treatment.

Suspending A at terminal: the resulting product from the above step is dissolved in 32 µl of buffer, 5 µl of Klenow buffer, 10 µl of 1 mM dATP and 3 µl of Klenow Exo are added into the mixture, and kept for 30 min at 37 (the reagents are provided by Illumina sample preparation kit PE-102-1001), the resulting product is purified by QIAGEN MinElute PCR purification kit (part #28004).

Connecting: the DNA is dissolved in 10 µl of buffer, 2×25 µl of DNA ligase buffer, 10 µl of PE Adapter Oligo Mix and 5 µl of DNA ligase are added to the mixture, and kept for 15 min at 20 (the reagents are provided by Illumina sample preparation kit PE-102-1001). The DNA is purified by QIAGEN QIAquick PCR purification kit (part #28104) after warm bath treatment.

FIG. 1 is a gel electrophoresis image, in which the DNA in a sample are prepared into a library for paired-end sequencing, the DNA in the library are subjected to electrophoresis by 1% of agarose gel, the most obvious stripe is located at 280 bp, due to containing 120 bp linker primers, the main DNA segments in the maternal plasma mainly focus at about 160 bp.

Preferably, PCR amplification can also be performed on the library for paired-end sequencing: 1 µl of DNA, 22 µl of pure water, 1 µl of PE PCR primer PE 2.0, 1 µl of PE to PCR primer PE 1.0 and 2× Phusion DNA polymerase (Finnzymes Oy) (the reagents are provided by Illumina sample preparation kit PE-102-1001). The DNA is amplified through PCR instrument, the procedure is 98, 30 s, 98, 40 s, 65, 30 s, 72, 30 s, 12 cycles in total, 72, 5 min.

Step 4: Sequencing the DNA sequencing library.

According to different libraries prepared in Step 3, paired-end short sequence sequencing, single-end long sequence sequencing or single-end short sequence sequencing can be performed respectively. The process for performing paired-end short sequence sequencing is as follows.

Single DNA molecule in DNA paired-end sequencing library is prepared into DNA cluster by cBot instrument of Illumina, this step also can be a step of changing single DNA molecule into polymolecule in a droplet by emulsion PCR. The generated DNA cluster or DNA droplet obtained by emulsion PCR is subjected to paired-end sequencing in Genome Analyzer or HiSeq2000 sequencer of Illumina. The process is automatically finished by the instrument itself.

Alternatively, the generated DNA cluster or DNA droplet obtained by emulsion PCR is subjected to single-end long sequence sequencing in Genome Analyzer or HiSeq2000 of Illumina, or SOLiD sequencer of Life Technologies. The sequencing steps and reaction conditions in Genome Analyzer or HiSeq2000 of Illumina, or SOLiD sequencer of Life Technologies are the same as above described.

Step 5: Determining which chromosome the DNA segment in the plasma comes from and determining whether the copy number of the chromosomes to be detected is normal.

After performing paired-end short sequence sequencing of the DNA library (alternatively, measuring single-end long sequence sequencing or single-end short sequence sequencing), when each 36 bp base sequence at each end of one DNA segment is known, the sequences on both ends can be compared with human genome standard sequence 37.1 (see the www Internet site at ncbi.nlm.nih.gov/projects/genome/assembly/grc/human/data/?build=37), which is also called hg19, to determine the respective position of the sequences at both ends on the chromosome. The distance between the sequences at both ends is the length of the DNA segment, at the same time, the chromosomal position of the sequences at both ends determine which chromosome the DNA segment comes from.

Figure 2:
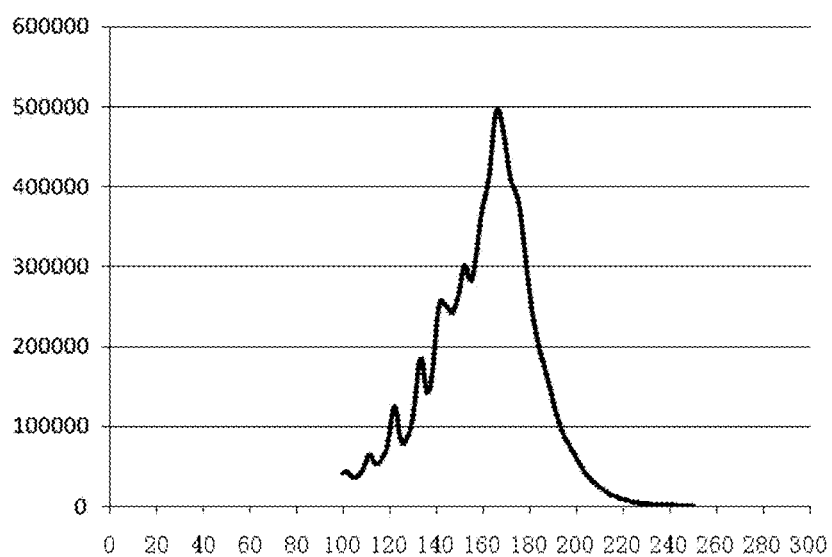
FIG. 2 is a distribution graph of DNA segment size of sample G356.

FIG. 2 is a distribution graph of DNA segment size of sample G356 determined according to the above method, from which short DNA in the maternal plasma mainly focus on between 100 bp and 220 bp.

Figure 3:
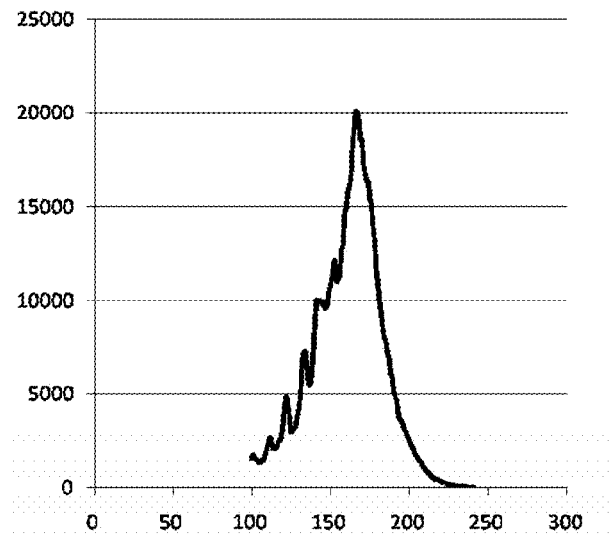
FIG. 3 is a distribution graph of DNA segment from X chromosome in a compared sample G356 made according to the segment size.
Figure 4:
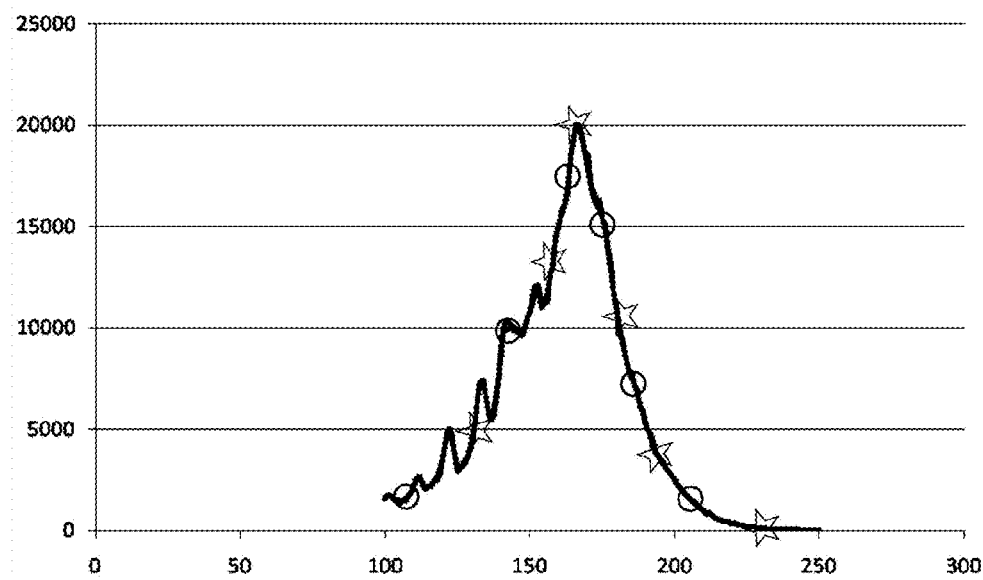
FIG. 4 is a distribution graph of calculated and actually measured DNA segments of X chromosome of G356 according to the segment size, in which the line with asterisk represents a graph obtained by multiplying the total number of DNA sequences of sample G356 by percent of X chromosome, circle represents the sequence number of X chromosomes actually measured. As shown in figure, the DNA segment distribution of G356 X chromosome calculated is the same as the actually measured distribution essentially, these two lines are basically consistent with each other.
Figure 5A:
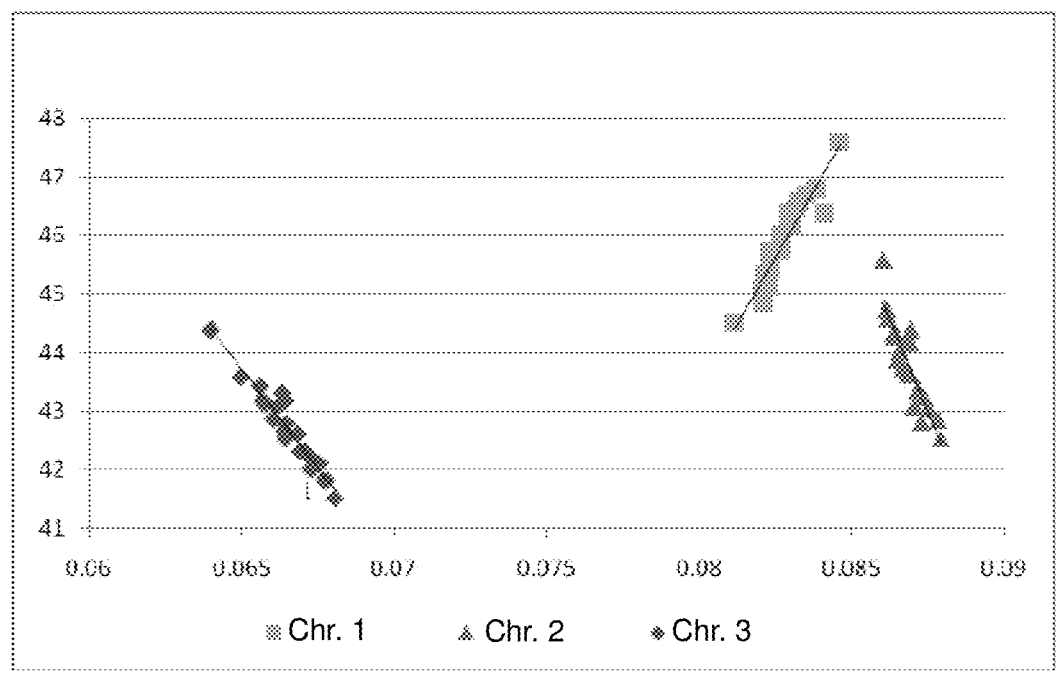
FIGS. 5A-5H are standard curves drawn according to the GC contents of the DNA segments from the chromosomes to be detected in G356, G397 (repeated for 8 times), G426, G735, G756, G760, G763, G770, G778, G779, G780, G781, G824 and G825 and the ratios of the DNA segments from the chromosomes to be detected to the total DNA segments, in which samples G356, G397, G426, G735, G756, G760, G763, G770, G778, G779, G780, G781, G824 and G825 are identified as normal female fetus samples [46, XX] through amniocentesis by chromosome karyotype in Xiangya Medical College of Central South University. X axis presents the ratio of the number of the DNA segments from the chromosomes to be detected to the total DNA segments, Y axis represents the GC content of DNA segments from the chromosomes to be detected. Each of 5A-5F shows standard curves of three chromosomes, orderly showing standard curves of the 1-th to the 18-th chromosomes.
Figure 5B:
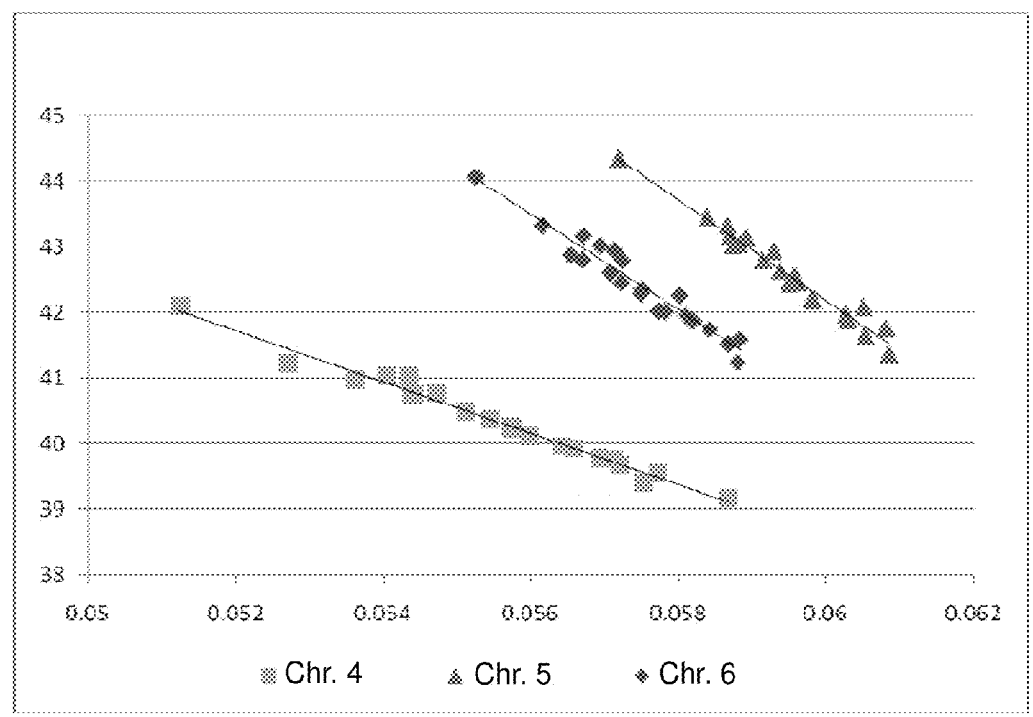
Figure 5C:
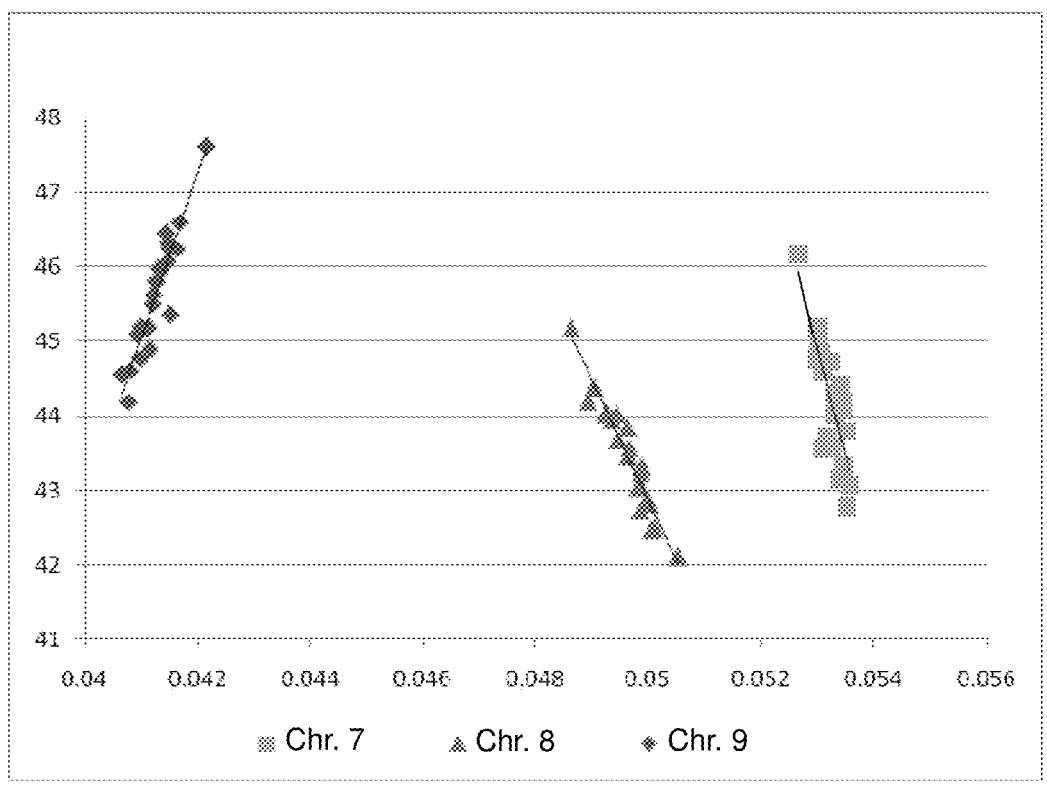
Figure 5D:
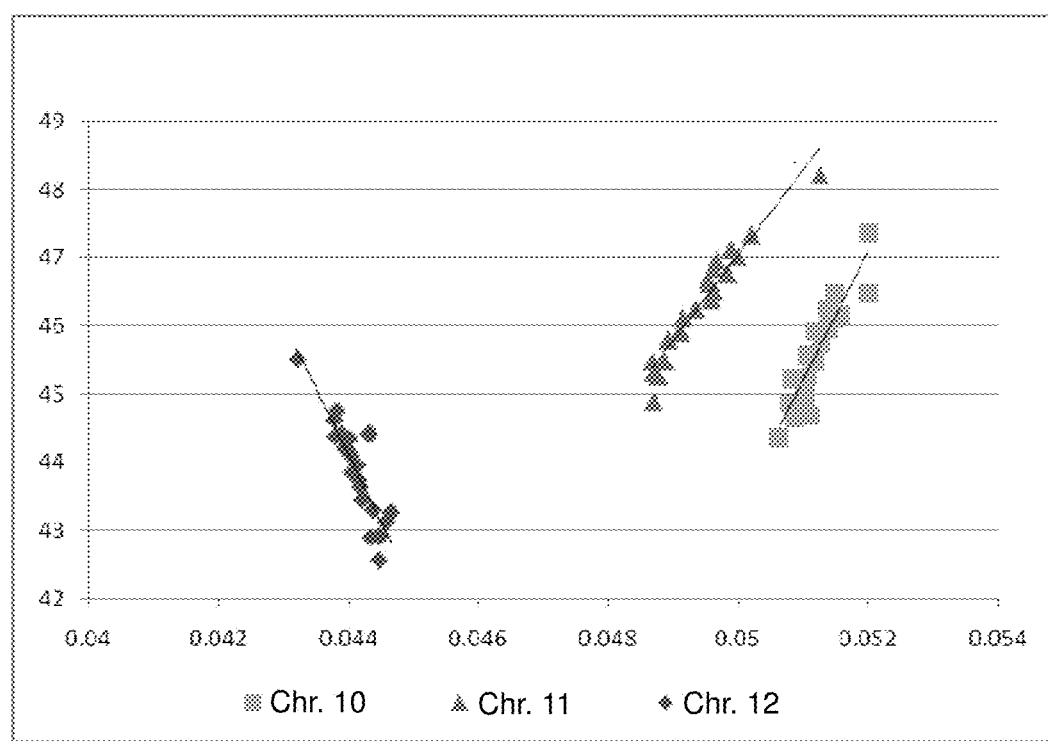
Figure 5E:
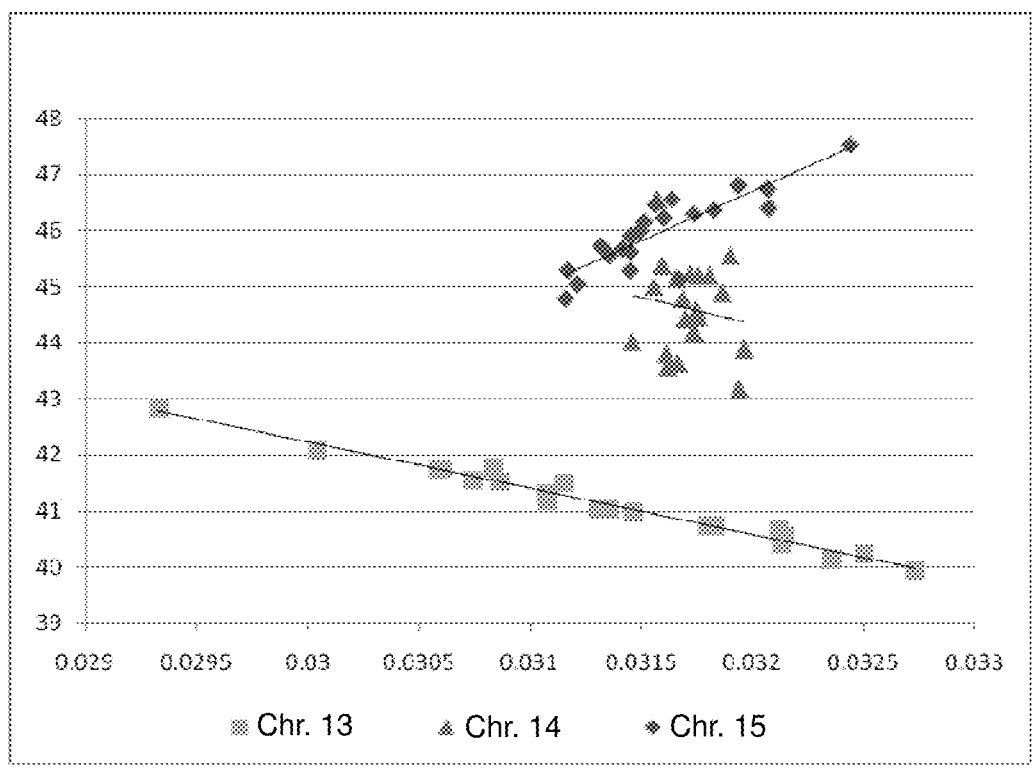
Figure 5F:
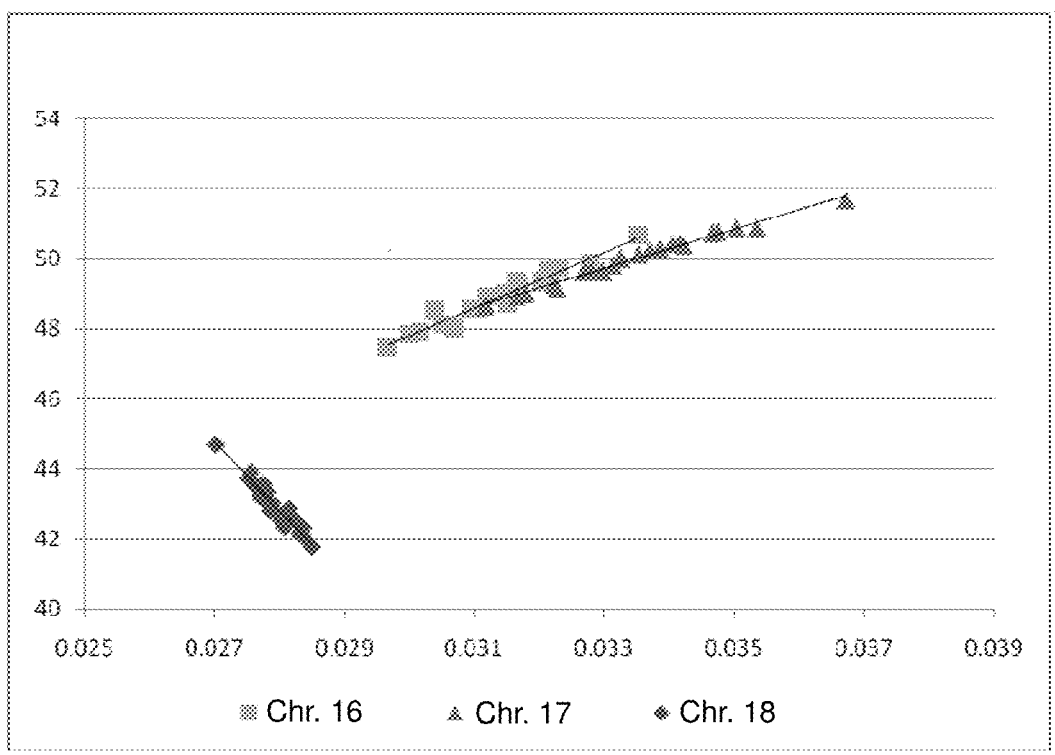
Figure 5G:
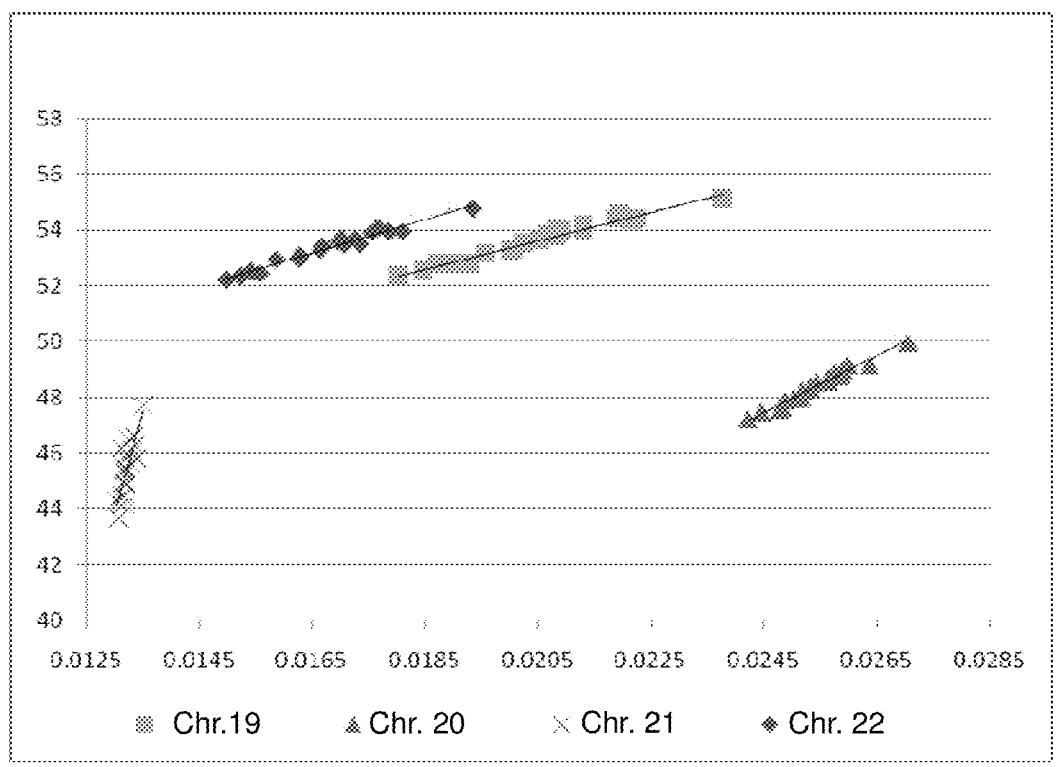
Figure 5H:
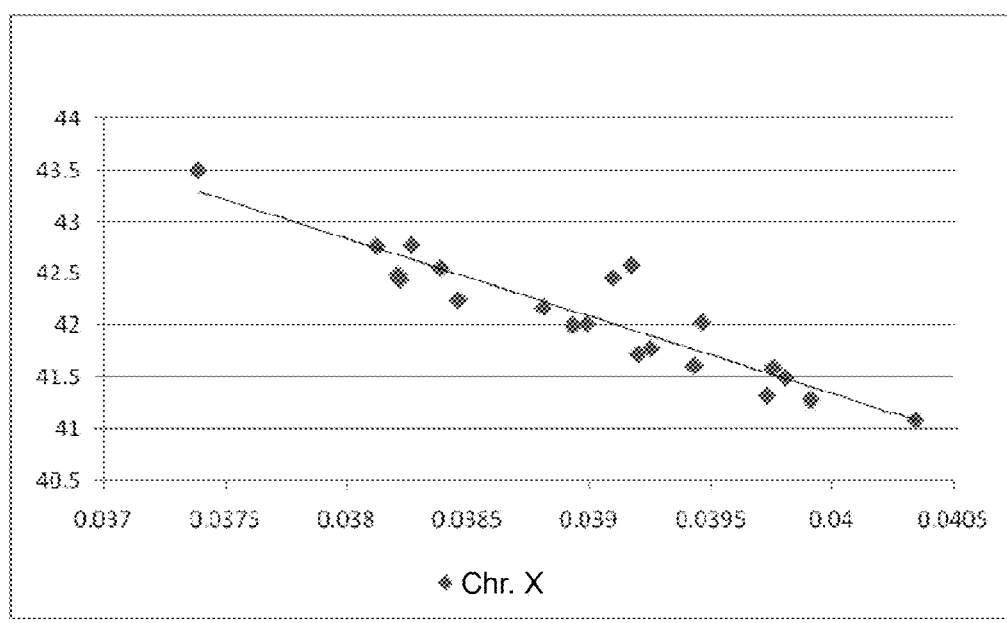

FIG. 3 is a distribution graph of DNA segment from X chromosome in a compared sample G356 made according to the segment size. The obtained graph is substantially the same as FIG. 2.

Step 6: Calculating the ratio of the number of DNA segments from the chromosomes to be detected to all DNA segments in the DNA in the same sample, correcting the ratio according to the GC content of the DNA segments from the chromosomes to be detected, and calculating the variation of the corrected ratio of the DNA segments from the chromosomes to be detected in a sample to be detected, and determining the copy number of the chromosomes to be detected according to degree of variation.

Preferably, the method includes calculating the ratio of the number of the DNA segments from the chromosomes to be detected in all DNA with length at any point or in any interval within the range of 100 bp to 250 bp in the same sample to the total number of all DNA segments with length at any point or in any interval within the range of 100 bp to 250 bp by sequencing and comparison results of all DNA with length at any point or in any interval within the range of 100 bp to 250 bp DNA sequence length, correcting the ratio according to the GC content of the DNA segments from the chromosomes to be detected, and calculating the variation of the corrected ratio of the DNA segments from the chromosomes to be detected in the sample to be detected, and determining the copy number of the chromosomes to be detected according to degree of variation.

In experiments, it is found that the accuracy of experimental result can be improved by sequencing and comparison results of all DNA with length at any point or in any interval within the range of 100 bp to 250 bp DNA sequence length.

The specific algorithm is as follows: Using standard samples, calculating the ratio of the DNA segments from the chromosomes to be detected in the same sample to all DNA segments, obtaining the GC content of the DNA segment from the chromosomes to be detected according to the sequencing results; drawing a standard curve of GC content (Y axis) and the percentage (X axis) of each chromosome or partial chromosome to all chromosomes according to the above ratio and GC content; correcting the measured ratio of chromosome of sample to be detected into a fixed GC value (usually arithmetic mean of GC value) according to its own function of the chromosome; and calculating the variation value Z of the corrected ratio of the DNA segments from the chromosomes to be detected in the sample to be detected, and determining the copy number of the chromosomes to be detected according to Z value.

FIGS. 5A-5H are standard curves drawn according to the GC contents of the DNA segments from the chromosomes to be detected in measured samples and the ratios of the DNA segments from the chromosomes to be detected to the total DNA segments. It can be seen from the figures that the GC contents of the DNA segments from chromosomes 2, 3, 4, 5, 6, 7, 8, 12, 13, 14, 18 and X are respectively in inverse proportion to the ratios of the DNA segments from each chromosome to the total DNA segments, the linear relationship linear relationships with the ratios of the DNA segments from each chromosome to the total DNA segments, the linear relationship can be represented by y=ax+b, where y represents the GC content of the DNA segment from the chromosome to be detected, x represents the ratio of the number of the DNA segments from the chromosome to be detected to the total DNA, a and b are constants, and a is negative. It should be noted that, with respect to different reference samples, small changes may occur in specific parameters of the formula, but the overall trend is unchanged. The functions of chromosomes 2, 3, 4, 5, 6, 7, 8, 12, 13, 14, 18 and X are shown in Table 1:

TABLE 1

| Chromosome No. | Function |
| --- | --- |
| 2 | Y = −1274.5X + 154.48 |
| 3 | Y = −682.68X + 88.11 |
| 4 | Y = −391.42X + 62.075 |
| 5 | Y = −772.25X + 88.517 |
| 6 | Y = −729.61X + 84.354 |
| 7 | Y = −2874.7X + 197.28 |
| 8 | Y = −1599.4X + 122.84 |
| 12 | Y = −1936.7X + 129.32 |
| 13 | Y = −827.29X + 67.049 |
| 14 | Y = −933.9X + 74.22 |
| 18 | Y = −1946.4X + 97.323 |
| X | Y = −749.77X + 71.33 |

The GC contents of the DNA segments from chromosomes 1, 9, 10, 11, 15, 16, 17, 19, 20, 21 and 22 are respectively in proportion to the ratios of the DNA segments from each chromosome to the total DNA segments, the linear relationship can be represented by y=ax+b, where y represents the GC content of the DNA segment from the chromosome to be detected, x represents the ratio of the number of the DNA segments from the chromosome to be detected to the total DNA, a and b are constants, and a is positive.

TABLE 2

| Chromosome No. | Function |
| --- | --- |
| 1 | Y = 909.17X − 29.372 |
| 9 | Y = 2211.3X − 45.632 |
| 10 | Y = 1886.8X − 51.026 |
| 11 | Y = 1255X − 15.714 |
| 15 | Y = 1775.8X − 10.124 |
| 16 | Y = 797.17X + 23.883 |
| 17 | Y = 560.83X + 31.227 |
| 19 | Y = 513.79X + 43.088 |
| 20 | Y = 1006.7X + 22.818 |
| 21 | Y = 7298X − 51.083 |
| 22 | Y = 596.24X + 43.346 |

Then, the measured ratio of chromosome of sample to be detected is corrected into a fixed GC value (usually arithmetic mean of GC value) according to its own function of the chromosome.

For example, it can be seen from the function y=ax+b represented by GC contents of the DNA segments from each chromosome and the ratios of the DNA segments from each chromosome to the total DNA segments that, the ratio x of the DNA segments from each chromosome to the total DNA segments in each sample can be corrected through the function according to GC value. The correction formula can be $$x = \bar{e} - \frac{(y - \hat{y})}{a},$$

where x is the corrected ratio of the DNA segments from each chromosome to the total DNA segments; $\bar{e}$ is the ratio of the specified chromosome segment to the total DNA segments in the detected sample; y is the GC content of the specified chromosome segment in the sample to be detected; $\hat{y}$ is arithmetic mean GC value of the chromosome segment in detected standard sample (known normal sample, such as 14 known normal standard samples detected in Embodiment 1). a is the slope of this curve. For the function of each chromosome, see Table 1 and Table 2; For different samples, e and ŷ are measured values of this test, which vary along with different samples to be detected.

Through calculating average values of these corrected X values and standard errors, value Z is obtained: Z=(corrected ratio x of sample to be detected−corrected average value of ratio of each standard sample)/standard error. The variation of the corrected ratio x in each sample to be detected is calculated, and the copy number of the chromosomes to be detected or partial chromosomes to be detected is determined according to value Z of variation. In general, the absolute value of Z being smaller than 3 is considered as normal detection error, and the absolute value of Z being bigger than 3 is considered to be abnormal.

The following Tables 3, 4 and 5 show detection and correction results of chromosomes 13, 18 and 21 calculated by detecting samples G356, G397 (repeated for 8 times), G426, G735, G756, G760, G763, G770, G778, G779, G780, G781, G824 and G825 with the method of Embodiment 1.

TABLE 3

Correction table of chromosome 13

| Sample | X | Y | Corrected X |
|---|---|---|---|
| G356 | 0.032128056 | 40.40838593 | 0.0312599 |
| G397L1 | 0.031796287 | 40.74129367 | 0.031330538 |
| G397L2 | 0.031829498 | 40.74485255 | 0.031368051 |
| G397L3 | 0.031300856 | 41.02955526 | 0.031183548 |
| G397L4 | 0.031461675 | 40.97527314 | 0.031278753 |
| G397L5 | 0.030861045 | 41.52415988 | 0.031341599 |
| G397L6 | 0.031076999 | 41.18977275 | 0.031153357 |
| G397L7 | 0.030740791 | 41.5445585 | 0.031246002 |
| G397L8 | 0.031068253 | 41.29163215 | 0.031267736 |
| G426 | 0.032116722 | 40.65542488 | 0.031547179 |
| G735 | 0.030833804 | 41.76349467 | 0.031603657 |
| G756 | 0.032145341 | 40.54153095 | 0.031438126 |
| G760 | 0.032505467 | 40.22754276 | 0.031418714 |
| G763 | 0.03135526 | 41.028428 | 0.03123659 |
| G770 | 0.029324725 | 42.84226241 | 0.031398557 |
| G778 | 0.030580783 | 41.74167735 | 0.031324265 |
| G779 | 0.030604185 | 41.75611311 | 0.031365114 |
| G780 | 0.03115125 | 41.49762797 | 0.031599733 |
| G781 | 0.030039316 | 42.09062396 | 0.031204592 |
| G824 | 0.032731055 | 39.92248585 | 0.031275559 |
| G825 | 0.032354852 | 40.14196058 | 0.03116465 |
| Average value | 0.03133363 | 41.1266026 | 0.03133363 |
| Standard error | 0.000853052 | 0.714097704 | 0.000131819 |
| Slope | −827.2898903 | | |

TABLE 4

Correction table of chromosome 18

| Sample | X | Y | Corrected X |
|---|---|---|---|
| G356 | 0.028355 | 42.32462 | 0.028009403 |
| G397L1 | 0.028042 | 42.66689 | 0.027871871 |
| G397L2 | 0.028211 | 42.5936 | 0.028003058 |
| G397L3 | 0.027866 | 42.92468 | 0.027828101 |
| G397L4 | 0.028163 | 42.8853 | 0.028105316 |
| G397L5 | 0.027723 | 43.42382 | 0.027941782 |
| G397L6 | 0.027887 | 43.01112 | 0.027893673 |
| G397L7 | 0.027615 | 43.52203 | 0.027884151 |
| G397L8 | 0.027718 | 43.18862 | 0.027815666 |
| G426 | 0.028085 | 42.34471 | 0.027749591 |
| G735 | 0.027524 | 43.74306 | 0.027906323 |
| G756 | 0.028028 | 42.56583 | 0.027805722 |

TABLE 4-continued

Correction table of chromosome 18

| Sample | X | Y | Corrected X |
|---|---|---|---|
| G760 | 0.028321 | 42.13679 | 0.02787838 |
| G763 | 0.027859 | 42.81759 | 0.027766269 |
| G770 | 0.027028 | 44.70943 | 0.027907267 |
| G778 | 0.02775 | 43.55682 | 0.028036728 |
| G779 | 0.02766 | 43.52168 | 0.027929435 |
| G780 | 0.027819 | 43.34723 | 0.027998124 |
| G781 | 0.027553 | 43.88948 | 0.028010923 |
| G824 | 0.02851 | 41.7596 | 0.027874031 |
| G825 | 0.028393 | 42.02757 | 0.027894578 |
| Average value | 0.02791 | 42.99812 | 0.027910019 |
| Standard error | 0.000353 | 0.710198 | 0.0000921681 |
| Slope | −1946.44 | | |

TABLE 5

Correction table of chromosome 21

| Sample | X | Y | Corrected X |
|---|---|---|---|
| G356 | 0.01313 | 44.40818 | 0.013271072 |
| G397L1 | 0.013154 | 44.93124 | 0.013223969 |
| G397L2 | 0.013215 | 44.89741 | 0.013289069 |
| G397L3 | 0.013191 | 45.45013 | 0.013189714 |
| G397L4 | 0.013192 | 45.39349 | 0.013197949 |
| G397L5 | 0.013315 | 46.10443 | 0.013224459 |
| G397L6 | 0.013301 | 45.56648 | 0.013283986 |
| G397L7 | 0.013347 | 46.32729 | 0.013225833 |
| G397L8 | 0.01339 | 45.78404 | 0.013342788 |
| G426 | 0.013157 | 44.51204 | 0.013283828 |
| G735 | 0.013269 | 46.54507 | 0.013117886 |
| G756 | 0.013212 | 44.89562 | 0.013286433 |
| G760 | 0.013046 | 44.22742 | 0.01321199 |
| G763 | 0.013181 | 45.2873 | 0.013202366 |
| G770 | 0.01351 | 47.67432 | 0.013203677 |
| G778 | 0.013235 | 45.93867 | 0.0131666 |
| G779 | 0.013146 | 46.1604 | 0.013047278 |
| G780 | 0.013177 | 45.80678 | 0.013126693 |
| G781 | 0.013333 | 46.55558 | 0.013180262 |
| G824 | 0.013081 | 43.62277 | 0.0133298 |
| G825 | 0.013164 | 44.15792 | 0.013339786 |
| Average value | 0.013226 | 45.44031 | 0.013225973 |
| Standard error | 0.000109 | 0.973152 | 0.0000762249 |
| Slope | 7298.004 | | |

Note that, the above detection and calculation method is not only suitable for detecting the copy number abnormality of the whole chromosome, but also suitable for detecting the copy number abnormality of the partial chromosome.

Below is an embodiment in which the copy number of fetal chromosome 13 in a sample to be detected is detected.

As described above, a total of 15 maternal blood samples are extracted, plasma samples from which blood cells are removed are obtained after centrifuging the blood samples at high speed, and each sample has a plasma volume of about 1 ml. The sample code is G352, G362, G372, G383, G397 (repeated for 8 times), G402, G409, G415, G424, G445, G440, G503, G588, G735 and G783. The above samples are collected by Professor Wu Lingqian from Xiangya Medical College of Central South University.

Figure 6:
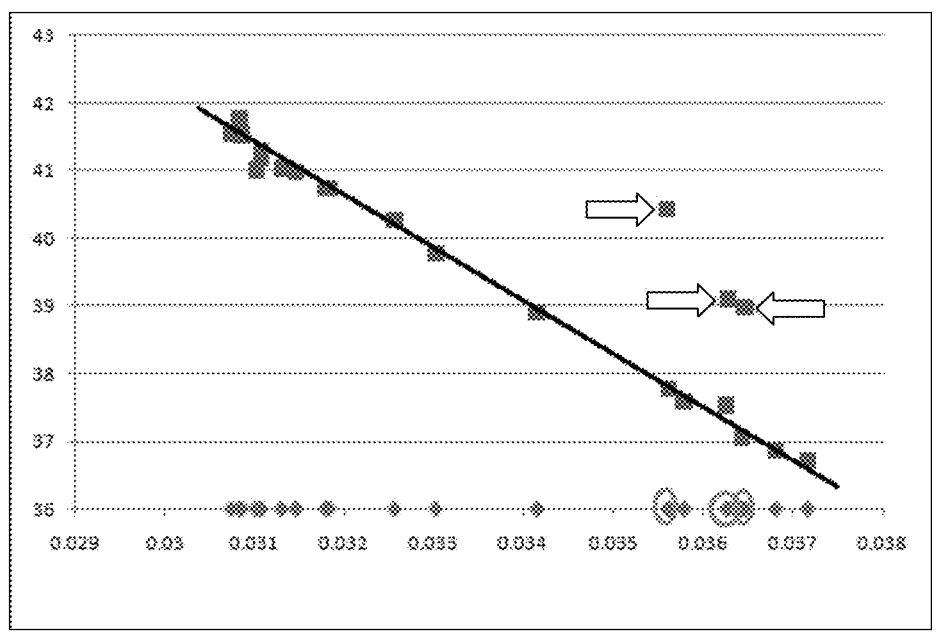
FIG. 6 is a schematic diagram of a sample of trisomy 13 detected by the method of the invention, in which X axis represents the ratio of the number of DNA segments from chromosome 13 to the total DNA segments, Y axis represents the GC content of the DNA segments from chromosome 13. The diamond on the X axis shows the ratio of the number of the DNA segments from chromosome 13 to the total DNA segments in each sample, the rectangle indicated by arrow represents a sample of trisomy 13 detected after correcting the GC content of DNA segments from chromosome 13. If the correction of the GC content of DNA segments from the chromosomes to be detected of the present invention does not be performed, three abnormal samples indicated by arrow cannot be found only by the ratio of the DNA segments from chromosome 13 to the total DNA segments, and there would be a false negative result.

The trisomy 13 which is possibly present is detected. The detection result is verified by standard curve of chromosome 13 obtained above. As shown in FIG. 6, in the absence of GC correction (marked with diamond on the X axis in the figure), it is impossible to distinguish trisomy 13 samples G445, G352 and G402 (samples marked with 3 circles on the x axis) from normal samples (samples without marks on the x axis). However, in the presence of GC correction (represented by rectangle in the figure), it is possible to clearly distinguish trisomy 13 samples G445, G352 and G402 (samples marked with 3 arrows in the figure) from normal samples (other samples represented by rectangle in the figure). The GC correction result is the same as the result identified by Professor Wu Lingqian from Xiangya Medical College of Central South University through amniocentesis by chromosome karyotype. As a result, the correction of GC content can be used for detecting trisomy 13 to reduce the occurrence of false negative result.

The following Table 6 only illustrates the detection and calculation result of part of samples to be detected, and does not illustrate the result of other samples.

TABLE 6

Calculation table of Z value of corrected chromosome 13

| Sample | Karyotype result | Corrected X | Corrected Z value |
| --- | --- | --- | --- |
| G445 | 47, XX, +13 | 0.033854 | 19.12307 |
| G352 | 47, XY, +13 | 0.033835 | 18.97637 |
| G402 | 47, XY, +13 | 0.034761 | 25.99744 |
| G383 | 46, XY | 0.031641 | 2.331371 |
| G415 | 47, XX, +18 | 0.031497 | 1.23855 |
| G503 | 46, XY | 0.031504 | 1.29343 |
| G424 | 47, XY, +18 | 0.031567 | 1.771192 |

| Chromosome 13 | Corrected X |
| --- | --- |
| Average value | 0.031334 |
| Standard error | 0.000132 |

It can be seen from the above table that, the Z value of samples G445, G352, G402 is more than 3, which can be judged as trisomy 13. The Z value of other samples is between −3 and +3.

Below is an embodiment in which the copy number of fetal chromosome 18 in a sample to be detected is detected.

As described above, a total of 16 maternal blood samples are extracted, plasma samples from which blood cells are removed are obtained after centrifuging the blood samples at high speed, and each sample has a plasma volume of about 1 ml. The sample code is G362, G372, G383, G397 (repeated for 8 times), G407, G409, G415, G424, G442, G432, G445, G440, G595, G588, G735 and G783. The above samples are collected by Professor Wu Lingqian of Xiangya Medical College of Central South University.

Figure 7:
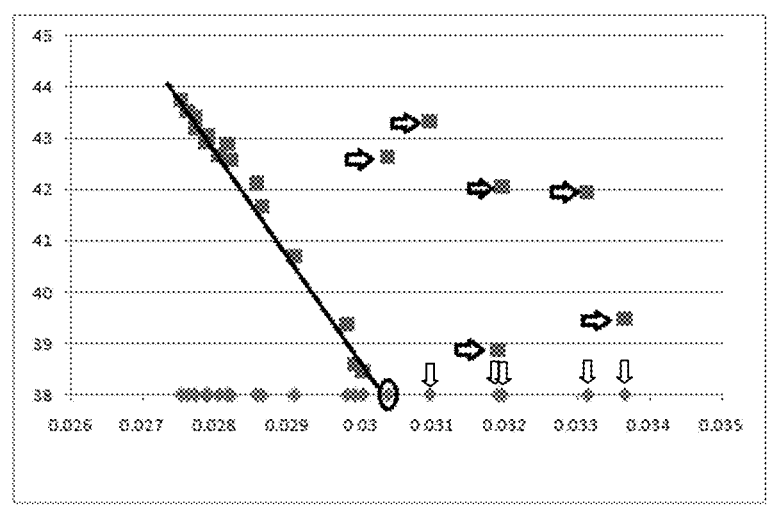
FIG. 7 is a schematic diagram of a sample of trisomy 18 detected by the method of the invention, in which X axis represents the ratio of the number of the DNA segments of chromosome 18 to the total DNA segments, Y axis represents the GC content of the DNA segments from chromosome 18. The diamond on the X axis shows the ratio of the number of the DNA segments from chromosome 18 to the total DNA segments in each sample, the rectangle indicated by arrow represents a sample of trisomy 18 detected after correcting the GC content of DNA segments from chromosome 18. If the correction of the GC content of DNA segments from the chromosomes to be detected of the present invention does not be performed, it is can be only found that 5 samples in which the ratio of the DNA segment from chromosome 18 to the total DNA segments is larger than or equal to 0.031 is the trisomy 18, and it cannot be found that two samples with a ratio of about 0.03 are abnormal, only by the ratio of the DNA segments from chromosome 18 to the total DNA segments, with respect to the two samples, there would be a false negative result.
Figure 8:
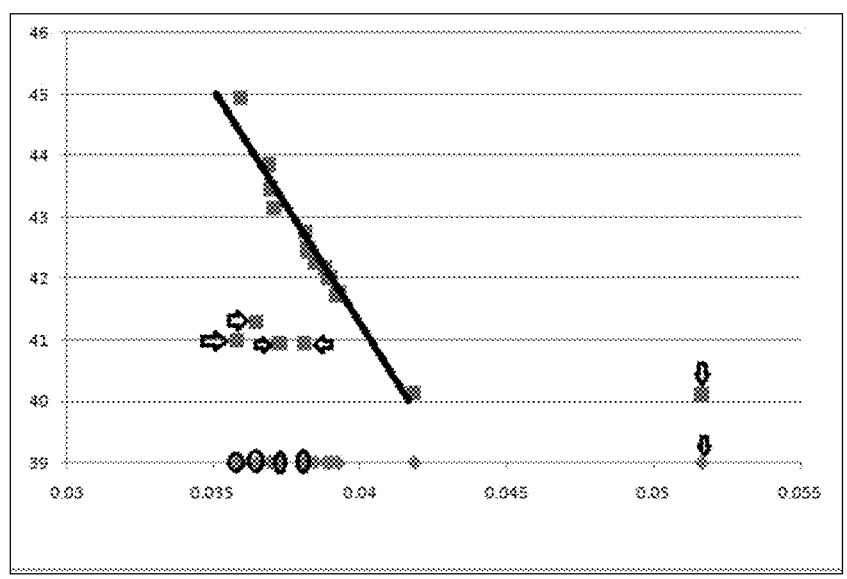
FIG. 8 is a schematic diagram of a sample of X monosomy or trisomy detected by the method of the invention, in which X axis represents the ratio of the number of the DNA segments of X chromosome to the total DNA segments, Y axis represents the GC content of the DNA segments from X chromosome. The diamond on the X axis shows the ratio of the number of the DNA segments from X chromosome to the total DNA segments in each sample, the rectangle indicated by arrow on the left of standard curve represents a sample of X monosomy detected after correcting the GC content of DNA segments from X chromosome, the rectangle indicated by arrow on the right of standard curve represents a sample of X trisomy detected after correcting the GC content of DNA segments from X chromosome. If the correction of the GC content of DNA segments from the chromosomes to be detected of the present invention does not be performed, one sample of X trisomy can only be found and the sample of X monosomy cannot be found easily only by the ratio of the DNA segments from X chromosome to the total DNA segments, and there would be a false negative result.

The trisomy 18 which is possibly present is detected. As shown in FIG. 7, the detection result is verified by standard curve of chromosome 18 obtained above. In the absence of GC correction (marked with diamond on the X axis in the figure), it is impossible to distinguish some trisomy 18 samples (samples marked with 1 back circle on the x axis) from normal samples (samples without marks on the x axis represented by diamond), which results in false negative samples. Other trisomy 18 samples (samples marked with down arrow on the X axis) can be detected without GC correction. However, in the presence of GC correction (represented by rectangle in the figure), it is possible to clearly distinguish all trisomy 18 samples (samples marked with horizontal arrows in the figure) from normal samples (other samples represented by rectangle in the figure). The GC correction result is the same as the result identified by Professor Wu Lingqian of Xiangya Medical College of Central South University through amniocentesis by chromosome karyotype. As a result, the correction of GC content can be used for detecting trisomy 18 to reduce the occurrence of false negative result.

The following Table 7 only illustrates the detection and calculation result of part of samples to be detected, and does not illustrate the result of other samples.

TABLE 7

Calculation table of Z value of corrected chromosome 18

| Sample | Karyotype result | Corrected X | Corrected Z value |
| --- | --- | --- | --- |
| G424 | 47, XY, +18 | 0.031846 | 42.7029466 |
| G442 | 47, XY, +18 | 0.03259 | 50.7813669 |
| G432 | 47, XY, +18 | 0.031475 | 38.6805289 |
| G415 | 47, XX, +18 | 0.029786 | 20.35574454 |
| G595 | 47, XY, +18 | 0.031124 | 34.87420168 |
| G407 | 47, XY, +18 | 0.030189 | 24.72396854 |
| G372 | 46, XY | 0.027704 | −2.234074343 |
| G383 | 46, XY | 0.027657 | −2.740277188 |
| G362 | 46, XY | 0.02795 | 0.428428385 |

| Chromosome 18 | Corrected X |
| --- | --- |
| Average value | 0.027910019 |
| Standard error | 0.0000921681 |

It can be seen from the above table that, the Z value of samples G424, G442, G432, G415, G595, G407 is more than 3, which can be judged as trisomy 18. The Z value of other samples is between −3 and +3.

Below is an embodiment in which the copy number of fetal chromosome 21 in a sample to be detected is detected.

As described above, a total of 14 maternal blood samples are extracted, plasma samples from which blood cells are removed are obtained after centrifuging the blood samples at high speed, and each sample has a plasma volume of about 1 ml. The sample code is G267, G387, G393, G376, G397 (repeated for 8 times), G405, G408, G409, G440, G491, G588, G641, G735 and G783. The above samples are collected by Professor Wu Lingqian of Xiangya Medical College of Central South University.

Figure 9A:
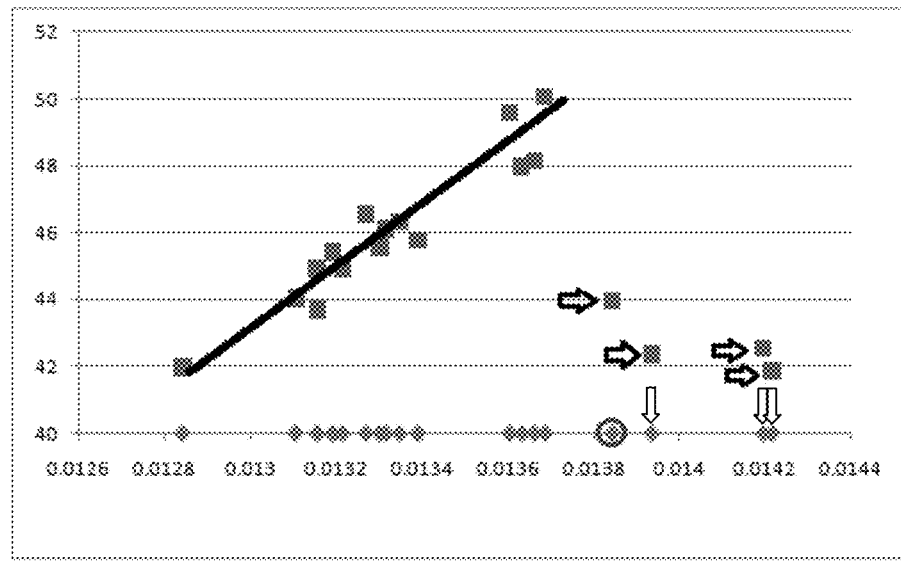
FIGS. 9A-9B are schematic diagrams of a sample of trisomy 21 detected by the method of the invention, in which X axis represents the ratio of the number of the DNA segments of chromosome 21 to the total DNA segments, Y axis represents the GC content of the DNA segments from chromosome 21. The diamond on the X axis shows the ratio of the number of the DNA segments from chromosome 21 to the total DNA segments in each sample, the rectangle indicated by arrow represents a sample of trisomy 21 detected after correcting the GC content of DNA segments from chromosome 18. If it is can be only found that 4 samples in which the ratio of the DNA segment from chromosome 21 in FIG. 9 to the total DNA segments is the maximum is the trisomy 21, and it cannot be found that the samples with a ratio of about 0.0138 are abnormal, only by the ratio of the DNA segments from chromosome 18 to the total DNA segments rather than by correcting the GC content of DNA segments from the chromosomes to be detected, with respect to the samples, there is a false negative result.
Figure 9B:
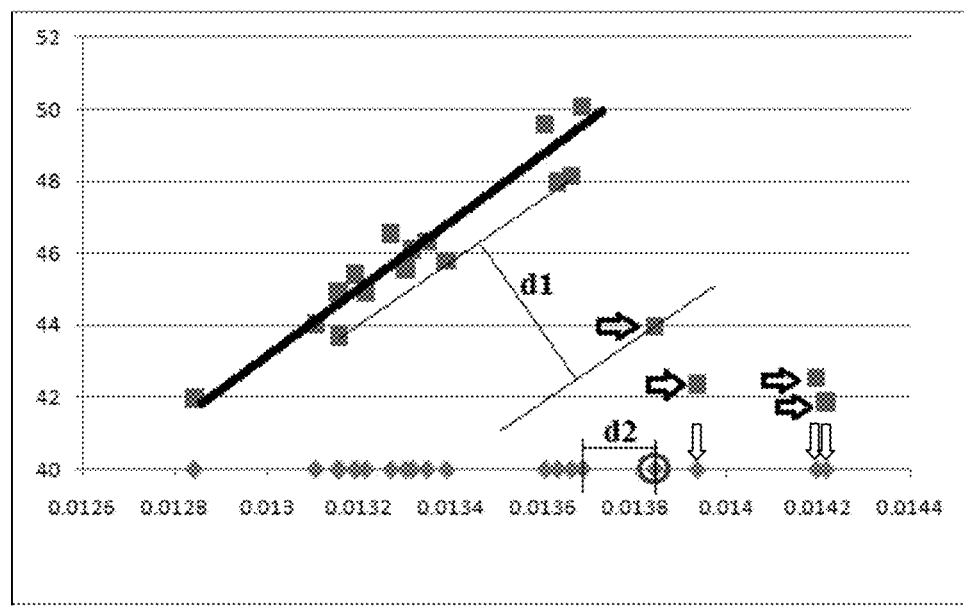

The trisomy 21 (i.e., Down's syndrome sample) which is possibly present is detected. As shown in FIG. 9A, the detection result is verified by standard curve of chromosome 21 obtained above. In the absence of GC correction (marked with diamond on the X axis in the figure), the trisomy 21 sample (1 sample marked with black circles and 3 vertical arrows on the x axis) can be detected only by the percentage of the trisomy 21 in all chromosomes. The difference between one sample (a sample marked with black circle on the x axis) and normal sample (other samples marketed with diamond) is not obvious, which may result in false negative samples. However, in the presence of GC correction (represented by rectangle in the figure), it is possible to clearly distinguish all trisomy 21 samples (samples marked with 4 horizontal arrows in the figure) from normal samples (other samples represented by rectangle in the figure). The GC correction result is the same as the result identified by Professor Wu Lingqian of to Xiangya Medical College of Central South University through amniocentesis by chromosome karyotype. The improvement of the accuracy of trisomy 21 by GC content correction can be measured by minimum distance between trisomy 21 and normal sample. As shown in FIG. 9B, the corrected minimum distance d1 is more than the minimum distance d2 which has not been corrected. As a result, the correction of GC content can be used for detecting trisomy 21 to reduce the occurrence of false negative result.

The following Table 8 only illustrates the detection and calculation result of part of samples to be detected, and does not illustrate the result of other samples.

TABLE 8

Calculation table of Z value of corrected chromosome 21

| Sample | Karyotype result | Corrected X | Corrected Z value |
|---|---|---|---|
| G405 | 47, XX, +21 | 0.014702324 | 19.36834952 |
| G387 | 47, XX, +21 | 0.014591238 | 17.91101164 |
| G376 | 47, XX, +21 | 0.014355433 | 14.81746245 |
| G393 | 47, XX, +21 | 0.014044123 | 10.73336561 |
| G491 | 46, XY | 0.013049564 | −2.314322329 |
| G641 | 46, XY | 0.013287067 | 0.801496645 |
| G488 | 46, XY | 0.013284892 | 0.772960653 |
| G408 | 46, XX | 0.013038312 | −2.461945144 |

| Chromosome 18 | Corrected X |
|---|---|
| Average value | 0.013225973 |
| Standard error | 0.0000762249 |

It can be seen from the above table that, the Z value of samples G405, G387, G376, G393 is more than 3, which can be judged as trisomy 21. The Z value of other samples is between −3 and +3.

Embodiment 2: A Kit for Detecting the Copy Number of Fetal Chromosomes or Tumor Cell Chromosomes With respect to the detecting method of Embodiment 1, the inventor of the application develops a kit for detecting the copy number of fetal chromosomes or tumor cell chromosomes, which includes:

an instrument for collecting blood from a pregnant women or a tumor patient, which can be any blood collecting needle for collecting blood, syringe or the like;

an instrument for separating blood cells from plasma in blood, which can be a micro-tube suitable for containing blood on a centrifuge or any other container or instrument for separation;

Reagents and instrument for extracting DNA from the plasma, which can include protease, saturated phenol, chloroform:isoamylol (24:1), sodium acetate, anhydrous alcohol, 70% ethanol, TE solution etc., the DNA in the plasma can be extracted by using DNA extraction kit produced by Qiagen (product number: 57704) and any other reagents or containers for extracting the DNA;

A reagent and an instrument for preparing the DNA into a sequencing library, the sequencing library can be a library for paired-end short sequence sequencing, a library for single-end long sequence sequencing or a library for single-end short sequence sequencing, the a reagent and an instrument for preparing the DNA into the library for paired-end short sequence sequencing includes: T4 DNA ligase buffer with 10 mM ATP, 10 mM dNTP Mix, T4 DNA polymerase, Klenow enzyme and T4 PNK (the above reagents are provided by Illumina sample preparation kit PE-102-1001), as well as ion exchange resin with affinity to the DNA under certain circumstances to realize the separation of DNA, also, QIAGEN QIAquick PCR product separation kit (product number: #28104) or QIAGEN MinElute PCR product separation kit (product number: #28004) can be selected;

A reagent and an instrument for sequencing the DNA, which can be used for performing paired-end short sequence sequencing, single-end long sequence sequencing or single-end short sequence sequencing on the DNA. The a reagent and an instrument for performing paired-end short sequence sequencing can include PE PCR primer PE 2.0, PE PCR primer PE1.0, Phusion DNA polymerase (Finnzymes Oy) (the reagents are provided by Illumina sample preparation kit PE-102-1001).

Embodiment 3: Another Kit for Detecting the Copy Number of Fetal Chromosomes or Tumor Cell Chromosomes The inventor of the application develops another kit for detecting the copy number of fetal chromosome or tumor cell chromosomes, which includes:

an instrument for collecting blood from a pregnant women or a tumor patient, which can be any blood collecting needle for collecting blood, syringe or the like;

an instrument for separating blood cells from plasma in blood, which can be a micro-tube suitable for containing blood on a centrifuge or any other container or instrument for separation;

A reagent and an instrument for extracting DNA from the plasma, which can include protease, saturated phenol, chloroform:isoamylol (24:1), sodium acetate, anhydrous alcohol, 70% ethanol, TE solution etc., the DNA in the plasma can be extracted by using DNA extraction kit produced by Qiagen (product number: 57704) and any other reagent or container for extracting the DNA;

A reagent and an instrument for separating the DNA with a physical method according to the size of the DNA segments, which can include: agarose powder (Biowest 11860), marker (Takara 100 bp DNA marker, product number: D505A) etc.; and A reagent and an instrument for sequencing DNA with length with length at any point or in any interval within the range of 100 bp to 250 bp, which can include a cutter for cutting agarose gel within a certain interval.

Preferably, the kit can include a reagent and an instrument for amplifying the DNA recovered from cut agarose gel and preparing it into a sequencing library.

Embodiment 4: A Device for Detecting the Copy Number of Fetal Chromosome or Tumor Cell Chromosomes A device for detecting the copy number of fetal chromosomes or tumor cell chromosomes includes:

a detecting module, which is used for sequencing DNA in a sample of maternal plasma or plasma of tumor patient, wherein the sequencing includes a step of preparing all DNA in the sample of maternal plasma or plasma of tumor patient into a sequencing library to sequence the DNA in the maternal plasma sample, the detecting module can includes cBot instrument of Illumina and Genome Analyzer or HiSeq2000 sequencer of Illumina or SOLiD sequencer of ABI;

a comparison module, which is used for comparing a sequencing result of the DNA with a genomic sequence map to determine which chromosome each DNA sequence comes from and the sequence length of each DNA segment, the comparison module can be human genome standard sequence database hg19;

a calculating module, which is used for calculating the ratio of the number of DNA segments from the chromosomes to be detected to all DNA segments in the same sample, correcting the ratio according to a GC content of the DNA segments from the chromosomes to be detected, and calculating the variation of the corrected ratio of the DNA segments from the chromosomes to be detected in a sample to be detected, and determining the copy number of the chromosomes to be detected according to degree of variation; and an output module, which is used for outputting the copy number of the chromosomes to be detected.

Optionally, the detecting module can detect all DNA segments in the sample, can also only detect all DNA with length at any point or in any interval within the range of 100 bp to 250 bp such as 150 bp to 175 bp, the detecting module can be a module or device for performing agarose gel electrophoresis by including a reagent and an instrument for separating the DNA in the maternal plasma according to the DNA segment size upstream of the detecting device.

Obviously, those skilled in the art should understand that some modules or some steps of the invention can be implemented by general computing devices. The modules or steps can be focused on a single computing device, or distributed on the network composed of multiple computing devices. Optionally, The modules or steps can be implemented by computing device executable program code, thereby storing them in a storage device and executing by the computing device, or implementing the modules or steps by making them into each integrated circuit module respectively, or making many of the modules or steps into single integrated circuit module. In such a way, the invention is not limited to the combination of any particular hardware and software.

The above is only the preferred embodiment of the invention and not intended to limit the scope of protection of the invention. For those skilled in the art, various variations and changes can be made to the invention. Any modifications, equivalent replacements, improvements and the like within the spirit and principle of the invention shall fall within the scope of protection of the invention.

REFERENCES

1. Cunningham F, et al. (2002) In Williams Obstretrics (McGraw-Hill Professional, New York), p 942.
2. Wapner R, et al. (2003) First-trimester screening for trisomies 21 and 18. N Engl J Med, 349:1405-1413.
3. Lo Y M, et al. (1997) Presence of fetal DAN in maternal plasma and serum. Lancet, 350: 485-487.
4. Lo Y M, et al. (2007) Plasma placental RNA allelic ratio permits noninvasive prenatal chromosomal aneuploidy detection. Nat Med, 13: 218-223.
5. Tong Y K, et al. (2006) Noninvasive prenatal detection of fetal trisomy 18 by epigenetic allelic ratio analysis in maternal plasma: Theoretical and empirical considerations. Clin Chem, 52: 2194-2202.
6. Fan H C, Quake S R. (2007) Detection of aneuploidy with digital polymerase chain reaction. Anal Chem, 79: 7576-7579.
7. Lo Y M, et al. (2007) Digital PCR for molecular detection of fetal chromosomal aneuploidy. Proc Natl Acad Sci USA, 104: 13116-13121.
8. Bentley D R, et al. (2008) Accurate whole human genome sequencing using reversible terminator chemistry. Nature, 456: 53-59.
9. McKernan K J, et al. (2009) Sequence and structure variation in a human genome uncovered by short-read, massively parallel ligation sequencing using two-base encoding. Genome Research, 119: 1527-1541.
10. Harris T D, et al. (2008) Single-molecule DNA sequencing of a viral genome. Science, 320: 106-109.
11. Fan H C, et al. (2008) Noninvasive diagnosis of fetal aneuploidy by sequencing DNA from maternal blood. Proc Natl Acad Sci USA, 105: 16266-16271.
12. Chiu R W K, et al. (2008) Noninvasive prenatal diagnosis of fetal chromosomal aneuploidy by massively parallel genomic sequencing of DNA in maternal plasma. Proc Natl Acad Sci USA, 105: 20458-20463.
13. Chiu R W K, et al. (2010) Maternal plasma DNA analysis with massively parallel sequencing by ligation for noninvasive prenatal diagnosis of trisomy 21. Chin Chem, 56:459-463.
14. Lewis D E, et al. (2010) Antigenic approach to the detection and isolation of microparticles associated fetal DNA. PCT, US2010, #025209.
15. Fan H C, et al. (2010) Analysis of the size distributions of fetal and maternal cell-free DNA by double-end sequencing. Clin Chem, 56: 1279-1286.

What is claimed is:

1. A method for detecting the copy number of a fetal chromosome or tumor cell chromosome, comprising the following steps:

collecting a maternal blood sample or a blood sample of a tumor patient;

separating a plasma sample from blood cells in the collected sample;

preparing DNA in the plasma sample into a DNA sequencing library by separating DNA segments according to size and forming a DNA sequencing library of DNA segments having a length within a range of 100 bp to 250 bp;

sequencing the DNA segments having a length within a range of 100 bp to 250 bp in the DNA sequencing library;

comparing a result of the sequencing step with a genomic sequence map to determine which chromosome each DNA sequence comes from and the length of each DNA sequence;

from the results of the sequencing step, calculating the ratio of the DNA segments from the chromosome to be detected to the total number of the DNA segments and determining the GC content of the DNA segments from the chromosome to be detected, correcting the ratio according to the GC content of the DNA segments from the chromosome to be detected, calculating the variation of the corrected ratio of the DNA segments from the chromosome to be detected in the plasma sample, and determining the copy number of the chromosome to be detected according to a degree of variation;

wherein the ratio according to a GC content of the DNA segments from the chromosome to be detected is corrected according to a function wherein the GC contents of the DNA segments from each chromosome respectively have linear relationships with the ratios of the DNA segments from each chromosome to the total DNA segments, and the linear relationship is represented by the formula y=ax+b, where y represents the GC content of the DNA segments from each chromosome respectively to be detected, x represents the ratio of the number of the DNA segments from each chromosome to be detected to the total DNA, a and b are constants, and a and b may be different values for different chromosomes;

wherein the correction function is the formula: corrected $x=\bar{e}-((y-\hat{y})/a)$, where corrected x is the corrected ratio of the DNA segments from the chromosome to be detected to the total DNA segments; $\bar{e}$ is the calculated ratio of the DNA segments from the chromosome to be detected to the total DNA segments in the plasma sample; y is the GC content of the DNA segments from the chromosome to be detected in the plasma sample; ŷ is an arithmetic mean GC value of the DNA segments from the chromosome to be detected in a detected standard sample, and a is the slope of the linear relationship represented by the formula y=ax+b; and wherein the method for detecting the copy number of a fetal chromosome or tumor cell chromosome is carried out by a device, which device comprises:

a reagent and instrument for physically separating DNA segments according to size and forming the DNA sequencing library of DNA segments having a length within a range of 100 bp to 250 bp;

a detecting module for sequencing DNA in the DNA sequencing library;

a comparison module for comparing a DNA sequencing result with a genomic sequence map to determine which chromosome each DNA sequence comes from and the length of each DNA sequence;

a calculating module for calculating the ratio of the number of DNA segments from the chromosome to be detected to the total number of DNA segments in the same sample, correcting the ratio according to a GC content of the DNA segments from the chromosome to be detected, calculating the variation of the corrected ratio of the DNA segments from the chromosome to be detected in a sample to be detected, and determining the copy number of the chromosome to be detected according to degree of variation; and an output module for outputting the copy number of the chromosome to be detected.

2. The method according to claim 1, wherein correcting the ratios of the chromosomes 2, 3, 4, 5, 6, 7, 8, 12, 13, 18 and X comprises the following linear relationship: the GC contents of the DNA segments from each of the chromosomes 2, 3, 4, 5, 6, 7, 8, 12, 13, 18 and X respectively have linear relationships with the ratios of the DNA segments from each chromosome to the total DNA segments, the linear relationship can be represented by y=ax+b, where y represents the GC content of the DNA segments from the chromosome to be detected, x represents the ratio of the number of DNA segments from the chromosome to be detected to the total DNA, a and b are constants, and a is negative; wherein the linear relationship between the GC contents of the DNA segments from each of the chromosomes 2, 3, 4, 5, 6, 7, 8, 12, 13, 18 and X and the ratios of the DNA segments from each chromosome to the total DNA segments is as follows:

| Chromosome No. | Function |
| --- | --- |
| 2 | y = −1274.5x + 154.48 |
| 3 | y = −682.68x + 88.11 |
| 4 | y = −391.42x + 62.075 |
| 5 | y = −772.25x + 88.517 |
| 6 | y = −729.61x + 84.354 |
| 7 | y = −2874.7x + 197.28 |
| 8 | y = −1599.4x + 122.84 |
| 12 | y = −1936.7x + 129.32 |
| 13 | y = −827.29x + 67.049 |
| 18 | y = −1946.4x + 97.323 |
| X | y = −749.77x + 71.33. |

3. The method according to claim 1, wherein correcting the ratios of the chromosomes 1, 9, 10, 11, 15, 16, 17, 19, 20, 21 and 22 comprises the following linear relationship: the GC contents of the DNA segments from each of the chromosomes 1, 9, 10, 11, 15, 16, 17, 19, 20, 21 and 22 respectively have linear relationships with the ratios of the DNA segments from each chromosome to the total DNA segments, the linear relationship can be represented by y=ax+b, where y represents the GC content of the DNA segments from the chromosome to be detected, x represents the ratio of the number of the DNA segments from the chromosome to be detected to the total DNA, a and b are constants, and a is positive.

4. The method according to claim 3, wherein the linear relationship between the GC contents of the DNA segments from each of the chromosomes 1, 9, 10, 11, 15, 16, 17, 19, 20, 21 and 22 and the ratios of the DNA segments from each chromosome to the total DNA segments is as follows:

| Chromosome No. | Function |
| --- | --- |
| 1 | y = 909.17x − 29.372 |
| 9 | y = 2211.3x − 45.632 |
| 10 | y = 1886.8x − 51.026 |
| 11 | y = 1255x − 15.714 |
| 15 | y = 1775.8x − 10.124 |
| 16 | y = 797.17x + 23.883 |
| 17 | y = 560.83x + 31.227 |
| 19 | y = 513.79x + 43.088 |
| 20 | y = 1006.7x + 22.818 |
| 21 | y = 7298x − 51.083 |
| 22 | y = 596.24x + 43.346. |

5. The method according to claim 1, wherein correcting the ratios of the chromosomes 2, 3, 4, 5, 6, 7, 8, 12, 13, 18 and X comprises the following linear relationship: the GC contents of the DNA segments from each of the chromosomes 2, 3, 4, 5, 6, 7, 8, 12, 13, 18 and X respectively have linear relationships with the ratios of the DNA segments from each chromosome to the total DNA segments, the linear relationship can be represented by y=ax+b, where y represents the GC content of the DNA segments from the chromosome to be detected, x represents the ratio of the number of the DNA segments from the chromosome to be detected to the total DNA, a and b are constants, and a is negative.

6. The method according to claim 1, wherein the DNA with length within the range of 100 bp to 250 bp is within the range of 150 bp-170 bp DNA.

7. The method according to claim 1, wherein the DNA with length within the range of 100 bp to 250 bp is the 167 bp DNA.

8. The method according to claim 1, wherein the modules are provided in a single computing device.

9. The method according to claim 1, wherein the modules are, or are distributed on a network composed of, multiple computing devices.

10. A method for determining a variation of a corrected ratio of DNA segments from a fetal chromosome or tumor cell chromosome to be detected in a plasma sample, comprising the following steps:

collecting a maternal blood sample or a blood sample of a tumor patient;

separating a plasma sample from blood cells in the collected sample;

preparing DNA in the plasma sample into a DNA sequencing library by separating DNA segments according to size and forming a DNA sequencing library of DNA segments having a length within a range of 100 bp to 250 bp;

sequencing the DNA segments having a length within a range of 100 bp to 250 bp in the DNA sequencing library;

comparing a result of the sequencing step with a genomic sequence map to determine which chromosome each DNA sequence comes from and the length of each DNA sequence;

from the results of the sequencing step, calculating the ratio of the DNA segments from the chromosome to be detected to the total number of the DNA segments and determining the GC content of the DNA segments from the chromosome to be detected, correcting the ratio according to the GC content of the DNA segments from the chromosome to be detected, and calculating the variation of the corrected ratio of the DNA segments from the chromosome to be detected in the plasma sample;

wherein the ratio according to a GC content of the DNA segments from the chromosome to be detected is corrected according to a function wherein the GC contents of the DNA segments from each chromosome respectively have linear relationships with the ratios of the DNA segments from each chromosome to the total DNA segments, and the linear relationship is represented by the formula $y=ax+b$, where y represents the GC content of the DNA segments from each chromosome respectively to be detected, x represents the ratio of the number of the DNA segments from each chromosome to be detected to the total DNA, a and b are constants, and a and b may be different values for different chromosomes;

wherein the correction function is the formula: corrected $x=\bar{e}-((y-\hat{y})/a)$, where corrected x is the corrected ratio of the DNA segments from the chromosome to be detected to the total DNA segments; $\bar{e}$ is the calculated ratio of the DNA segments from the chromosome to be detected to the total DNA segments in the plasma sample; y is the GC content of the DNA segments from the chromosome to be detected in the plasma sample; $\hat{y}$ is an arithmetic mean GC value of the DNA segments from the chromosome to be detected in a detected standard sample, and a is the slope of the linear relationship represented by the formula $y=ax+b$; and wherein the method for detecting the copy number of a fetal chromosome or tumor cell chromosome is carried out by a device, which device comprises:

a reagent and instrument for physically separating DNA segments according to size and forming the DNA sequencing library of DNA segments having a length within a range of 100 bp to 250 bp;

a detecting module for sequencing DNA in the DNA sequencing library;

a comparison module for comparing a DNA sequencing result with a genomic sequence map to determine which chromosome each DNA sequence comes from and the length of each DNA sequence;

a calculating module for calculating the ratio of the number of DNA segments from the chromosome to be detected to the total number of DNA segments in the same sample, correcting the ratio according to a GC content of the DNA segments from the chromosome to be detected, and calculating the variation of the corrected ratio of the DNA segments from the chromosome to be detected in a sample to be detected, and determining the copy number of the chromosome to be detected according to degree of variation.

* * * * *